US006683020B2

(12) United States Patent
Baird, Jr. et al.

(10) Patent No.: US 6,683,020 B2
(45) Date of Patent: Jan. 27, 2004

(54) NAPHTHENE RING OPENING OVER AN IRIDIUM RING OPENING CATALYST

(75) Inventors: William C. Baird, Jr., Baton Rouge, LA (US); Darryl P. Klein, Ellicott City, MD (US); Jingguang G. Chen, Hockessin, DE (US); Gary B. McVicker, Califon, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 09/897,194

(22) Filed: Jul. 2, 2001

(65) Prior Publication Data

US 2002/0040176 A1 Apr. 4, 2002

Related U.S. Application Data

(60) Provisional application No. 60/220,092, filed on Jul. 21, 2000.

(51) Int. Cl.[7] ............................................... B01J 21/12
(52) U.S. Cl. ........................................ 502/261; 502/327
(58) Field of Search ............................ 502/66, 232, 261, 502/327, 263

(56) References Cited

U.S. PATENT DOCUMENTS

| | | | |
|---|---|---|---|
| 3,617,485 A | 11/1971 | Kittrell | 208/59 |
| 3,617,511 A | 11/1971 | Jenkins et al. | 208/112 |
| 3,631,117 A | 12/1971 | Kovach et al. | 260/666 |
| 3,779,897 A | 12/1973 | Wrench et al. | 208/89 |
| 3,943,052 A | 3/1976 | Kmak et al. | 208/140 |
| 3,953,368 A | 4/1976 | Sinfelt | 252/466 |
| 4,018,670 A | 4/1977 | Sinfelt et al. | 208/140 |
| 4,046,673 A | 9/1977 | Paynter et al. | 208/140 |
| 4,134,823 A | 1/1979 | Bertolacini et al. | 280/65 |
| 4,140,626 A | 2/1979 | Bertolacini et al. | 208/216 |
| 4,224,192 A | 9/1980 | Foster et al. | 252/466 B |
| 4,757,041 A * | 7/1988 | Oleck et al. | 502/65 |
| 4,783,575 A | 11/1988 | Schmidt et al. | 585/748 |
| 4,834,866 A | 5/1989 | Schmidt | 208/65 |
| 4,956,075 A | 9/1990 | Angevine et al. | 208/120 |
| 5,015,614 A | 5/1991 | Baird, Jr. et al. | 502/250 |
| 5,026,950 A | 6/1991 | Schmidt et al. | 585/737 |
| 5,334,792 A | 8/1994 | Del Rossi et al. | 585/314 |
| 5,345,026 A | 9/1994 | Chang et al. | 585/700 |
| 5,463,155 A | 10/1995 | Galperin et al. | 585/310 |
| 5,763,731 A | 6/1998 | McVicker et al. | 585/737 |
| 5,770,042 A | 6/1998 | Galperin et al. | 208/65 |
| 5,811,624 A | 9/1998 | Hantzer et al. | 585/700 |
| 5,888,922 A | 3/1999 | Galperin | 502/163 |
| 5,906,728 A | 5/1999 | Iaccino et al. | 208/61 |
| 5,925,239 A | 7/1999 | Klein et al. | 208/213 |
| 5,928,498 A | 7/1999 | McVicker et al. | 280/213 |
| 5,935,420 A | 8/1999 | Baird, Jr. et al. | 208/213 |
| 5,993,642 A | 11/1999 | Mohr et al. | 208/46 |
| 6,057,486 A * | 5/2000 | Merlen et al. | 585/481 |
| 6,221,240 B1 | 4/2001 | Klein et al. | 208/213 |
| 2001/0056032 A1 * | 12/2001 | Loic et al. | 502/64 |

OTHER PUBLICATIONS

Schultz and co–workers (Proc. 5th Intl. Catal. Congr., North–Holland Publ. (Aidam), v.2, 1229–39, (1973), no month.
Egan, et al., J. Amer. Chem. Soc., 84, 1204–12 (1962), no month.
Gault, et al., Adv. Catal., 30, 1–95, (1981), no month.
Weitkamp, et al., in Structure and Reactivity of Modified Zeolites, Elsevier (Adam), 279–90, (1984), no month.
Sergienko, et al., Khim. Geol. Nauk., 2, 65–70 (1976), no month.

* cited by examiner

*Primary Examiner*—Stanley S. Silverman
*Assistant Examiner*—Edward M. Johnson
(74) *Attorney, Agent, or Firm*—Gerard J. Hughes; Jeremy J. Kliebert

(57) ABSTRACT

Disclosed is a process for opening naphthenic rings of naphthenic ring-containing compounds, along with catalysts which can be used in that process. The ring opening is accomplished using a ring opening catalyst comprising Ir on a composite support of alumina and acidic silica-alumina molecular sieve. The ring opening activity is not significantly deactivated by exposure to oxygen at greater than about 250° C.

7 Claims, No Drawings

US 6,683,020 B2

NAPHTHENE RING OPENING OVER AN IRIDIUM RING OPENING CATALYST

CROSS REFERENCE TO RELATED APPLICATION

This case claims benefit of U.S. Provisional Patent Application No. 60/220,092 filed Jul. 21, 2000.

FIELD OF THE INVENTION

This invention relates to a method and composition for opening naphthenic rings of naphthenic ring-containing compounds. In particular, this invention relates to the use of a catalyst composition comprising Ir on a composite support of alumina and an acidic silica-alumina molecular sieve.

BACKGROUND OF THE INVENTION

Ir-containing ring opening catalysts are useful in converting multi-ring aromatics by reduction to naphthenes, and then ring opening the naphthenes to paraffins. For example, in U.S. Pat. No. 5,763,731, a ring opening catalyst is disclosed which contains a metal function and an acid function. The metal function is supplied by Ir, Ru, or Rh. The acid function, supplied by a zeolitic material, is effective for isomerizing six-membered naphthenic rings to five-membered naphthenic rings. The metal function is effective for ring opening naphthenic rings, particularly the five-membered naphthenic rings. Paraffin content of diesel, jet fuel, and heating oil, as well as light cycle oil, compositions can be creased in a variety of ways in order to increase cetane number. For example Ir catalysts have been shown to be highly effective in ring opening naphthene ring-containing compounds contained in diesel, jet fuel, heating oil, and light cycle oil compositions, which results in increased paraffin content and, therefore, higher cetane. See for example, U.S. Pat. No. 5,811,624. Such catalysts are useful for upgrading the quality of mid-distillate petroleum streams by providing improvements in gravity, volume, and cetane number. Further improvements, particularly higher cetane number, are nevertheless desired. Conventional IR-containing ring opening catalysts which have been used to ring open naphthene rings of naphthene ring-containing compositions found in diesel, jet fuel, heating oil, and light cycle oil compositions tend, however, to deactivate over time. It is believed that this deactivation is due to deposition of heavy carbonaceous residues on the catalyst during the ringing opening process. Removal of these residues would, therefore, be required to maintain, or restore, activity. Ideally, regeneration by a simple carbon burn in the presence of oxygen would be a desired method. There is also a desire to find a ring opening catalyst that can be regenerated for extended use.

SUMMARY OF THE INVENTION

In one embodiment, the invention relates to a ring opening catalyst comprised of Ir on a composite support of an alumina component and an acidic silica-alumina molecular sieve component. The catalyst is resistant to deactivation by calcination in air and provides higher activity than conventional Ir on alumina catalyst. In addition, the composite catalyst has lower cracking activity and superior gas/liquid selectivity.

In a preferred embodiment, the catalyst is a naphthene ring opening catalyst which comprises Ir on a composite support of alumina and acidic silica-alumina molecular sieve, with the acidic silica-alumina molecular sieve preferably having a Si/Al atomic ratio of at least about 30, more preferably at least about 40, most preferably at least about 60, prior to compositing with the alumina. Preferably, the composite support's alumina component is present in a range of from about 99 to about 1 wt. %, and the acidic silica-alumina molecular sieve component is present in a range of from about 1 to about 99 wt. %; more preferably the alumina component is present in a range of from about 95 to about 5 wt. %, and the acidic silica-alumina molecular sieve component is present in a range of from about 5 to about 95 wt. %; most preferably, the alumina component is present in a range of from about 90 to about 10 wt. %, and the acidic silica-alumina molecular sieve component is present in a range of from about 10 to about 90 wt. %. The weight percents are based on the weight of the composite support.

In another preferred embodiment, the catalyst further comprises at least one other or "second" Group VIII metal selected from Pt, Pd, Rh, or Ru. Preferably, the second Group VIII metal or metals is present in a range of from about 0.01 to about 5 wt. %; more preferably, the second Group VIII metal is present in a range of from about 0.01 to about 2.0 wt. %; most preferably, the second Group VIII metal is present in a range of from about 0.01 to about 1.0 wt. %. The weight percents are based on the weight of the ring opening catalyst.

In yet another preferred embodiment, the Ir is present in a range of from about 0.01 to about 2.0 wt. %. Preferably, Ir is present in a range of from about 0.1 to about 1.2 wt. %. Most preferably, Ir is present in a range of from about 0.01 to about 1.0 wt. %. The weight percents are based on the weight of the ring opening catalyst.

In another embodiment, there is provided a process for opening naphthene rings of naphthene ring-containing compounds in a feed stream. The process comprises providing a naphthene ring-containing feed stream; and contacting the naphthene ring-containing feed stream with the naphthene ring opening catalyst of this invention.

Ring opening can be carried out at a temperature ranging from about 150° C. to about 400° C.; a total pressure ranging from about 100 to about 3,000 psig; a liquid hourly space velocity ranging from about 0.1 to about 10 V/V/Hr; and a hydrogen treat gas rate ranging from about 200 to about 10,000 standard cubic feet per barrel (SCF/B).

In another preferred embodiment, the feed stream is a petroleum feed stream which has a boiling point of from about 175° C. to about 600° C.

In a preferred embodiment, the ring opening process further comprises ring opening naphthene rings containing at least one tertiary carbon site at the tertiary carbon site, thereby forming a ring opened product having increased linear paraffin functionality relative to that of the feed stream. The process can also include recovering the ring opened product. The ring-opened product may be used directly, for example, as a diesel fuel, jet fuel, gas oil and heating oil, and it may be blended with other petroleum streams for use, for example, as a diesel fuel, jet fuel, gas oil, and heating oil. Preferably, the ring opened product is blended with a petroleum stream having a boiling point of from about 175° C. to about 600° C., wherein the blend has a cetane number of at least about 40.

Desirably, the naphthene ring-containing feed stream has a sulfur content of less than about 10 ppm, preferably less than about 1 ppm, more preferably less than about 0.1 ppm. It is also desirable that the naphthene ring-containing feed stream contains less than about 20 wt. % total aromatic compounds.

In yet another preferred embodiment, there is provided a method of making a naphthene ring opening catalyst. The method comprises mixing together an alumina component and an acidic silica-alumina molecular sieve component. The mixture is then composited, and Ir is added to the composite to form a naphthene ring opening catalyst. Other Group VIII metals can also be added to the composite.

The invention also relates to a naphthene ring opening catalyst system which comprises a naphthene ring isomerizing catalyst containing a catalytically active naphthene ring isomerization metal supported on a first catalyst support in an amount effective to isomerize a $C_6$ naphthene ring-containing compound to a $C_5$ naphthene ring-containing compound. The catalyst system further comprises the naphthene ring opening catalyst comprising Ir on a composite support of alumina and silica-alumina molecular sieve, including the preferred embodiments thereof.

Also included as part of this invention are the products made by the stated processes.

DETAILED DESCRIPTION OF THE INVENTION

A major parameter in defining the value of diesel and jet fuel range products is cetane number. In general, the higher the cetane, the higher the quality of diesel and jet fuel range products.

While paraffins are typically high in cetane number, linear paraffins are generally higher in cetane number than branched paraffins having a corresponding number of carbons. Therefore, linear paraffins are highly desirable in the blending and manufacturing of high cetane fuels.

The invention is based in part on the discovery of ring opening catalyst compositions useful in processes for forming high cetane number distillate having a desirable concentration of compounds, which have a high degree of linear paraffin functionality. More particularly, the catalyst compositions are useful for opening rings at tertiary carbon sites in naphthene or naphthenic ring-containing distillates in order to form products with a high degree of linear paraffin functionality. The compositions are especially effective in opening compounds containing $C_5$ and $C_6$ naphthene rings bearing at least one tertiary carbon.

As defined herein, compounds having a high degree of linear paraffin functionality have fewer paraffin (i.e., alkyl) side chains and longer paraffin substituents. According to this definition, linear paraffins, particulary $C_{10}$–$C_{20}$ linear paraffins, are the most highly desirable compounds for use as a diesel or jet fuel product, though other compounds having a relatively high degree of linear paraffin functionality are also acceptable. For example, a cycloalkane ring compound having a single, linear alkyl side chain has relatively high paraffin functionality compared to a cycloalkane ring having multiple side chains. By the same definition, an aromatic ring compound having a single, linear alkyl side chain has a relatively high linear paraffin functionality compared to an aromatic ring compound having multiple side chains.

It has been found that conventional Ir/alumina ring opening catalysts, such as those disclosed in U.S. Pat. No. 5,763,731, are deactivated by exposure to oxygen containing streams at temperatures well below those needed to accomplish an effective, efficient regeneration. Loss of ring opening activity has also been found to occur at temperatures less than about 300° C., and activity is greatly diminished at temperatures greater than about 400° C. This invention overcomes this difficulty by providing a regenerable catalyst, allowing for more efficient long term and repeated use.

One embodiment this provides is a ring opening catalyst comprising Ir. The Ir is supported on a composite support of an alumina component and an acidic silica-alumina molecular sieve component. The ring opening activity of the catalyst is not significantly deactivated by exposure to oxygen at greater than about 250° C.; cracking is lower than that of a standard Ir on alumina ring opening catalyst; and selectivity to liquids is higher. The catalyst of this invention, therefore, exhibits the ability to withstand the relatively high temperature ranges encountered during regeneration, such that it can be reused for extended periods of time.

Ir may be supported on the composite support by conventional impregnation procedures such as incipient wetness or absorption from aqueous solution. The Ir loading can range from about 0.01 to about 2.0 wt. %, preferably from about 0.1 to about 1.2 wt. %, more preferably from about 0.1 to about 1.0 wt. %.

In an alternative embodiment, the linear paraffin functionality of the ring opened product can be improved by adding to the Ir-containing catalyst at least one other or "second" Group VIII metal selected from Pt, Ru, and Rh, in an amount effective for opening a naphthene ring-containing compound at a tertiary carbon site. The combination of the Ir and the second Group VIII metal or memtals is particularly effective in ring opening a naphthene ring at a tertiary carbon site. This means that a product having a relatively high degree of linear paraffin functionality can be formed.

As defined herein, a tertiary carbon (3° carbon) is the site of location of a substituent group on a naphthenic ring compound. Tertiary carbons are represented by such structural features, for example, as —CH(R)—CH$_2$— and —H(R)—CH(R)— where R is a carbon-containing chain, preferably a $C_{1-C10}$ carbon-containing chain.

Opening the ring structure of naphthenic ring compounds at the tertiary carbon site, known as tertiary bond cleavage, is particularly desirable for $C_6$ naphthenic rings. Tertiary bond cleavage is advantageous because isomerization of the $C_6$ rings to $C_5$ rings is abated so that the ring-opened product will have a high degree of linear paraffin functionality.

In ring opening at a tertiary carbon site, it is preferred that the Ir-containing catalyst additionally comprise at least one of Pt and Rh. Pt is particularly preferred. The Ir content of these catalysts can range from about 0.3 to about 2 wt. %, preferably from about 0.5 to about 1.5 wt. %, more preferably from about 0.6 to about 1.2 wt. %, and most preferably from about 0.7 to about 1.0 wt. %. The content of the Pt, Ru, and Rh in the Ir-containing catalyst can range from about 0.001 to about 2.0 wt. %, preferably from about 0.005 to about 1.5 wt. %, more preferably from about 0.007 to about 1.3 wt. %, and most preferably from about 0.01 to about 0.8 wt. %. Preferred Ir catalyst compositions (wt. %) include 0.01Me-0.9Ir, 0.05Me-0.9Ir, 0.1Me-0.9Ir, 0.3Me-0.9Ir, and 0.6Me-0.9Ir where Me is at least one of Pt, Rh, and Ru. The metal weight percents are based on the weight of the catalyst.

The composite support is a composite of an alumina component and an acidic silica-alumina molecular sieve component. As defined herein, a composite support is a mixture of the alumina component and the acidic silica-alumina molecular sieve. Ir, and optionally a second Group VIII metal, is deposited on the composite support such that the metal components will be distributed over both the alumina and silica-alumina molecular sieve components. However, the metals can be deposited separately on both the alumina component and the silica-alumina molecular sieve compent, and then the composite formed.

The amounts of the two components in the composite support preferably range from about 99 to about 1 wt. % alumina and from about 1 to about 99 wt. % acidic silica-alumina molecular sieve. More preferably, the alumina is present in a range of from about 95 to about 5 wt. %, and the acidic silica-alumina molecular sieve is present in a range of from about 5 to about 95 wt. %. Most preferably, the alumina is present in a range of from about 90 to about 10 wt. %, and the acidic silica-alumina molecular sieve is present in a range of from about 10 to about 90 wt. %. Weight percents of support components are based on the weight of the support. The alumina and acidic silica-alumina molecular sieve components can be composited by combining together as a dry mixture of finely divided powders, as a slurry mixture in an appropriate medium, preferably water, by spray drying, by commingling upstream of the extruder, and other techniques common to the preparation of composite materials.

The alumina component can be selected from typical commercial aluminas normally utilized as catalyst supports. The physical and chemical specifications of the alumina selected are to be appropriate for the eventual end use application as determined by feed character and reactor limitations.

In a particularly preferred embodiment, the alumina support is prepared by digesting high purity alumina hydrate powder in a weak organic acid, thereby forming an alumina sol which is then spray-dried by a conventional spray-drying technique to produce the alumina hydrate powder. A more complete description of this process is described in U.S. Pat. No. 5,015,614, which is incorporated herein by reference.

The acidic silica-alumina molecular sieve component is selected from those materials whose ring isomerization of methylcyclohexane is characterized by substantial isomerization to ethylcyclopentane relative to isomerization to polyalkylated cyclopentanes, such as dimethylcyclopentanes. As used herein, substantial isomerization to ethylcyclopentane means that at least about 50 wt. % of isomerized product will be to ethylcyclopentane.

Preferably, the acidic silica-alumina molecular sieve is a faujasite type zeolite having a Si/Al atomic ratio of at least about 30, preferably at least about 40, more preferably at least about 60. Particularly preferred acidic silica-alumina molecular sieves are ECR-4, ECR-30, ECR-32, ECR-35, and their equivalents, with ECR-32 being most preferred. These acidic silica-alumina molecular sieves are described in detail in U.S. Pat. Nos. 4,714,601; 4,879,103; 4,931,267; and 5,116,590, the descriptions of each being incorporated herein by reference. The Si/Al ratios of these silica-alumina molecular sieves can be increased using known dealumination techniques, such as that described in U.S. Pat. No. 5,763,731, the description of which is incorporated by reference.

In one embodiment, the metals can be supported on a modified composite substrate of alumina and acidic silica-alumina molecular sieve. The modified composite substrate can be prepared by incorporating therein an effective amount of modifier into the composite substrate. The modifier is such that, when used in an effective amount, it contributes to the resulting ring opening catalyst an improved overall selectivity to provide a product having a high degree of linear paraffin functionality, with simultaneous suppression of isomerization reactions, when compared to an identical catalyst not containing such modifiers. The term "effective amount of modifier" as used herein refers to the concentration range of modifier which, when used in a ring opening process, will improve the selectivity to provide a product having a high degree of linear paraffin functionality and reduce isomerization of linear paraffins. It should be noted that the modifiers are incorporated into the alumina component only, and not into the composite support once formed. The modifier should not be added to the acidic silica-alumina component.

Preferred elements that can be incorporated as modifiers into the composite substrate for the purposes of this invention include one or more of Cs, Mg, Ca, and Ba. Ca, Mg, and Ba are more preferred, with Mg being most preferred.

Generally, the modifier concentration will be at least about 0.1 to about 50 wt. %. Preferably, the modifier concentration will be about 0.5 to about 40 wt. %, more preferably about 1 to about 30 wt. %, and most preferably about 2 to about 25 wt. %. The modifier component can be incorporated into the alumina component of the substrate during any stage of production.

The modifier elements are preferably added to the alumina component as aqueous solutions of their common salts, preferably nitrates, nitrites, oxides, hydroxides, halides, carboxylates, and the like using either incipient wetness or absorption from solution techniques. Incipient wetness is a preferred procedure.

The modified support compositions of this invention are also characterized as having: (i) a surface area greater than about 50 m$^2$/g, preferably from about 100 to about 700 m$^2$/g, and more preferably from about 100 to about 300 m$^2$/g; (ii) a bulk density from about 0.3 to about 1 g/ml, preferably from about 0.4 to about 0.8 g/ml; (iii) an average pore volume from about 0.2 to about 1.1 ml/g, preferably from about 0.3 to about 0.8 ml/g; and (iv) an average pore diameter from about 30 to about 300 Angstroms.

The addition of the metals (i.e., Ir or the other Group VIII metals) to the support material can be accomplished by conventional techniques. Preferred techniques include incipient wetness impregnation and absorption from excess aqueous solution. Alternatively, the metals may be incorporated into the support material during its preparation as disclosed in U.S. Pat. No. 4,963,249, the description of which is incorporated herein by reference.

The metals can also be added in precursor form. Suitable metal precursors are the halides, the halometallic acids, nitrates, nitrites, amine halo complexes, amine nitrate complexes, and amine nitrite complexes. Metal deposition from organic solvents may also be practiced using organometallic complexes such acetylacetonates, carbonyls and the like. Preferably, Ir is added as a soluble salt or complex of Ir, such as halides, haloiridic acids, acetylacetonates, nitrates, and the like. Chloroiridic acid is particularly preferred.

Decomposition of the deposited complexes can be accomplished thermally in an air, hydrogen, or inert atmosphere by conventional heating, or by the application of microwave or ultrasonic radiation. The catalyst may be dried in air, or dried from about 100 to about 120° C. for from about 1 to about 24 hours. The catalyst can be calcined in air at a temperate greater than about 250° C. for about 1 to about 24 hours, preferably at greater than about 300° C. for about 1 to about 6 hours, and more preferably greater than about 350° C. for about 1 to about 4 hours, and most preferably for about 400° C.±about 25° C. for about 3 hours. The calcination may be conducted at atmospheric pressure or at pressures ranging up to about 400–600 psig. Air is a preferred oxygen source, but oxygen diluted with a suitable inert to give oxygen concentrations ranging from about 1 vol. % to 25 vol. % is acceptable. The catalysts may be activated by conventional methods. For example, the catalysts can be reduced in hydrogen at about 400° C. to about 500° C. for about 1 to about 24 hours, preferably about 400° C. to about 500° C. for about 1 to 12 hours, more preferably about 450° C. to about 500° C. for about 1 to about 5 hours at pressures ranging from atmospheric to about 400 psig to about 600 psig.

In another embodiment, the ring opening, Ir-containing catalyst may be combined with a naphthene ring isomerizing catalyst to form a ring opening catalyst system. The isomerizing catalyst contains a catalytically active naphthene ring isomerization metal supported on a catalyst support in an amount effective to isomerize a $C_6$ naphthene ring-containing compound to a $C_5$ naphthene ring-containing compound. The catalytically active naphthene ring isomerization metal is preferably at least one of Pt and Pd. The preferred Pt, Pd, and Pd—Pt-containing catalyst has high selectivity for isomerizing $C_6$ to $C_5$ naphthene rings, and a low selectivity for isomerizing linear paraffin chains to branched paraffin chains.

The dual catalyst arrangement of this invention allows product to be formed which has a high degree of linear paraffin functionality. The isomerization catalyst and the ring opening catalyst may be mixed together or provided in a stacked bed arrangement. In one embodiment, the isomerizing catalyst contains 0.1 to 10.0 wt. % Pt, Pd, or a combination thereof Preferably, the ring opening catalyst contains 0.01 0.5 wt. % Ir. The isomerization and ring opening metals may be present at a weight ratio of 50–99 parts of isomerization metal to 50–1 parts of ring opening metal. Consequently, Ir may be loaded onto the substrate at an amount that is substantially less than the amount used in conventional Ir-only ring opening catalysts.

The naphthene ring isomerizing catalyst and the naphthene ring opening catalyst combination may be arranged in either a mixed bed or stacked bed configuration relative to one another. In the stacked bed configuration it is preferred that the naphthene ring isomerizing catalyst occupy the upstream, or lead, position, while the naphthene ring opening catalyst occupies the downstream, or tail, position. In either the stacked or mixed bed configuration the catalyst charge is desirably distributed in such a manner that the bed is rich in the naphthene ring isomerizing component and lean in the naphthene ring opening component. In a preferred embodiment, the weight ratio of the isomerization component of the ring opening component can range from about 50 to about 99 parts by weight of the isomerization component and about 50 to about 1 parts by weight of the ring opening component, preferably about 50 to about 95 parts by weight of the isometric component and about 50 to about 5 parts by weight of the ring opening component, and more preferably about 50 to about 90 parts by weight of the isomerization component and about 50 to about 10 parts by weight of the ring opening component. The parts by weight are based on the total weight of the catalyst bed.

As discussed, it is desirable to minimize the Ir content of the catalyst system. Therefore, it is preferred that the If loadings of the ring opening component be drawn from the lower end of the preferred ranges. Isomerization metal loadings for the isomerization component, conversely, may be drawn from the high end of the preferred ranges. Representative, but not limiting Ir loadings may fall in the range from about 0.01 to about 0.5 wt. %; for Pt and Pd these values may range from about 0.1 to about 1.0 wt. %.

The metals (i.e., at least one of Pt and Pd) of the isomerizing catalyst may be supported on conventional refractory supports. Particularly desirable supports are refractory inorganic oxides. Non-limiting examples of refractory inorganic oxides include alumina, silica, zirconia, titania, chromia, zinc oxide, magnesia, thoria, boria, silica-alumina, silica-magnesia, chromia-alumina, alumina-boria, silica-zirconia, and combinations thereof. Alumina is a preferred support.

As discussed, the catalysts and catalyst systems of the invention are useful for upgrading petroleum streams such as middle distillate. Accordingly, a feedstream which is to be contacted with the catalyst of this invention will typically contain a mix of hydrocarbons having one or more of the naphthene ring-containing compositions, and the naphthene ring-containing compositions preferably contain at least one alkyl substituent. Preferably, the feedstream will comprise at least about 5 wt. % of at least one naphthenic ring-containing compound, more preferably at least about 25 wt. %, most preferably at least about 50 wt. %. Typically the feedstream will comprise from about 5 to about 85 wt. % of at least one naphthenic ring-containing compound.

As used herein, a naphthene or a naphthenic ring-containing composition refers to a cycloalkane or a composition containing at least one cycloalkane ring in its structure. For example, the term can refer to either a $C_5$ or $C_6$ ring-membered cycloparaffin. The cycloparaffin can also include various side chains, particularly one or more alkyl side chains of 1–10 carbons. In addition the cycloparaffin can be attached or fused to other ring structures, forming two or three membered ring compounds. The additional ring members can be saturated or unsaturated, as long as at least one ring of the complete structure contains a tertiary carbon. The ring structure containing the tertiary carbon should be saturated. Examples of two and three membered ring structures which can contain a tertiary carbon include saturated or partially saturated naphthalenes, indenes, fluorenes, phenanthrenes, anthracenes, acenaphthalenes, and biphenylenes.

In a more preferred embodiment, the hydrocarbon containing the naphthene ring compositions that are to be opened will include $C_5$ and $C_6$ naphthene ring compounds that do not include additional ring members. Nonlimiting examples of these compounds include methylcyclopentanes, ethylcyclopentanes, propylcyclopentanes, butylcyclopentanes, pentylcyclopentanes, methylcyclohexanes, ethylcyclohexanes, propylcyclohexanes, butylcyclohexanes, and pentylcyclohexanes. Preferably, the $C_5$ and $C_6$ ring naphthene ring compounds contain alkyl substituents.

Naphthenic ring-containing compounds are found in a wide variety of hydrocarbon feeds. For example, these compounds can be contained in petroleum streams boiling in the distillate range. These streams will typically include a variety of chemical compounds, including multi-ring compositions. Preferably, this invention uses a petroleum feed stream which has an average boiling point of from about 175° C. to about 600° C. Examples of such a feed stream include diesel fuel, jet fuel, heating oil, gas oil, and light cycle oil. Gas oil includes vacuum gas oil boiling in the range of from about 340° C. to about 565° C., which is typically derived from vacuum distillation of crude oil, or it can be obtained by conversion of products such as coker gas oil or heavy cat cycle oil. Other feed streams can also be used if appropriately pre-treated. These streams include chemical feed streams and lube streams.

To convert naphthene compounds to paraffins, a catalytically effective amount of at least one catalyst of this invention is contacted with an appropriate feed stream under catalytic ring opening conditions. Such conditions are such that the $C_5$ and $C_6$ rings of the naphthene compounds are opened when contacted with the catalyst. Suitable process conditions include temperatures from about 150° C. to about 400° C., preferably from about 225° C. to about 350° C.; a total pressure from about 100 to 3,000 psig, preferably from about 100 to about 2,200 psig; more preferably about 100 to about 1,500 psig; a liquid hourly space velocity of about 0.1 to about 10 V/V/Hr, preferably from about 0.5 to about 5 V/V/Hr; and a hydrogen treat gas rate of from about 200 to about 10,000 standard cubic feet per barrel (SCF/B), preferably 500 to 5000 SCF/B. SCF/B means standard cubic feet per barrel, and V/V/Hr means volume of feed per volume of catalyst per hour.

The catalyst may be regenerated utilizing conventional procedures of calcining and reducing. The spent catalyst is initially freed of feedstock by stripping with hydrogen, or a suitable inert gaas such as nitrogen, at temperatures and pressures sufficient for removal of residual feed from the bed. Representative temperatures range from about 200° C. to about 600° C., preferably from about 250° C. to about 500° C., and more preferably from about 270° C. to about 400° C. Representative pressures range from about one atmosphere to about 800 psig. Oxygen levels may range from about 0.5 to about 20 vol. %. The bed temperature is then lowered to a level compatible with the admission of air, or some other oxygen-containing gas, to the reactor containing the catalyst. The oxygen content may be controlled by the use of inert diluents to vary the oxygen level in the treat gas as the regeneration proceeds. Conditions may be regulated as in the regeneration of conventional catalytic reforming catalysts in order to avoid achieving temperatures higher than the catalyst deactivation temperature. Carbonaceous residues may be purged by combustion by controlling the temperature, oxygen content, and times as required to substantially remove the residue. At the conclusion of the oxygen burn, the bed is purged with a suitable inert gas such as nitrogen prior to being returned to service. Reduction may be carried out at about 200° C. to about 500° C. for about one to about 24 hours at pressures ranging from about 1 atmosphere to about 800 psig.

Conventional ring opening reactors may be used in the ring opening process of this invention. A fixed bed reactor system wherein the feedstock is passed over one or more stationary beds of catalyst is preferred. Multiple reactors can be used in either series or parallel configurations.

Hydrogen gas (i.e., a hydrogen-containing treat gas) conducted to the reaction process may flow over the catalyst either in a direction cocurrent or countercurrent with the feedstock. Hydrogen is supplied to saturate the carbons where ring opening occurs, and it is preferably supplied in stoichiometric excess. In one embodiment, reactor effluent is passed to a separation zone where hydrogen that has not been consumed in the reaction process can is separated off and can be recycled to the reaction zone together with make-up hydrogen as needed or cascaded to a lower pressure unit for further processing. In another embodiment, the treat gas is employed in a "once through" arrangement and is therefore not recycled.

Countercurrent reactors incorporating the catalyst are a preferred embodiment, since properly constructed countercurrent reactors can provide better contacting of reactants and treat gas and provide better removal of $H_2S$ which may be present. Such a reactor is disclosed in U.S. Pat. No. 5,942,197, the description of which is incorporated herein by reference. This preferred design is less susceptible to flooding than conventional countercurrent reactors because it incorporates passageways to bypass one or more catalyst beds. Bypass of at least a portion of the hydrogen treat gas is designed to occur when the pressure differential across the catalyst bed increases to a predefined threshold correlating to a near-flood condition. When gas bypasses the catalyst bed, the pressure differential across the catalyst bed decreases to permit the downward flow of liquid. When the pressure differential falls below a predefined level, the bypassing of gas is automatically stopped.

It is preferred that the feed streams be hydrotreated prior to ring opening to reduce sulfur content to low levels, preferably less than about 10 ppm, more preferably less than about 1 ppm, most preferably less than about 0.1 ppm. This is particularly desirable when high sulfur feeds are used in the ring opening process, since the ring opening catalysts are sensitive to high sulfur content.

Hydrotreating to reduce sulfur is referred to herein as hydrodesulfurization. Conventional hydrodesulfurization catalysts may be used to reduce the sulfur content of feed containing sulfur compounds to the preferred levels.

Nonlimiting examples of conventional hydrodesulfurization catalysts which may be used to reduce the sulfur content of the feed include catalysts which comprise a Group VI metal with one or more Group VIII metals as promoters, the metals being on a refractory support. Conventional hydrodesulfurization processes are conducted at pressures ranging from about 50 to about 2000 psig; preferably from about 100 to about 1500 psig; a liquid hourly space velocity ranging from about 0.2 to about 6 V/V/Hr; and a hydrogen gas rate of about 200 to 5000 SCF/B.

Sulfur sorbents, including regenerable sulfur sorbents, may also be used to reduce the sulfur content of the feed. These materials are capable of removing the easy sulfur compounds, particularly hydrogen sulfide, under relatively mild sulfur removing conditions. Examples of sulfur sorbents include metal oxides. These systems are disclosed in U.S. Pat. Nos. 5,928,498; 5,925,239; 5,935,420; 4,003,823; U.S. Pat. No. 4,007,109; U.S. Pat. No. 4,087,348; U.S. Pat. No. 4,087,349; U.S. Pat. No. 4,119,528; and U.S. Pat. No. 4,127,470, all of which are incorporated by reference herein.

If significant aromatic compounds are present in the feed stream, it is desirable to saturate them. It is preferred that the feedstock contain less than about 20 wt. % total aromatic compounds, preferably less than about 15 wt. %, more preferably less than about 10 wt. % available for ring opening.

The aromatics saturation (ASAT) process may be performed in one or a series of reactors either before or after the ring opening process, since either mode will generally result in a product having increased cetane number due to the lowering of the aromatic content. Saturation of aromatics in the feed is preferred, however, prior to the ring opening process. This is because saturation of aromatics tends to result in the formation of additional napththenes, providing additional material that can ultimately be converted using the catalyst of this invention to form compounds having a higher degree of linear paraffin functionality. In another preferred embodiment, a hydrodesulfurization reactor will be placed in front of the aromatics saturation reactor so that the catalyst in the aromatics saturation reactor will contact low sulfur feedstock.

Any conventional aromatic saturation process may be used to hydrogenate the aromatic rings of the aromatic compounds in connection with the invention. Typical conditions for saturating aromatics containing feedstocks include temperatures from about 150° C. to about 400° C., pressures from about 100 to about 2000 psig, space velocities from about 0.4 to about 6 V/V/Hr, and hydrogen gas rates from about 200 to about 6000 standard cubic feed per barrel (SCF/B). Lower temperatures are found to be most desirable for the hydrogenation or saturation reactions since nonselective cracking reactions thereby are minimized. Selective saturation of the aromatics results in a saturated intermediate from the hydrogenation zone usually containing less than 15 wt. % total aromatics.

Ring opening may also be practiced in a variety of stacked or mixed bed configurations along with aromatics saturation and sulfur removal. The stacked and mixed beds can occupy a single reactor or multiple reactors. Aromatics saturation and sulfur removal can take place in either cocurrent or countercurrent mode. The stacking of fixed beds of catalyst refers to the sequence of beds disposed with respect to the direction of flow of the liquid phase reactants. In a single reactor, such beds would be vertically disposed from top to bottom. In a series of reaction vessels the sequence is comparable as defined by the flow of the liquid phase.

A reactor may, for example, be loaded to have stacked layers of a sulfur reducing catalyst (e.g., a hydrodesulfurization (HDS) catalyst); a sulfur sorbent (sorbent); an aromatics saturation (ASAT) catalyst; and/or a ring opening (RO) catalyst. Specific examples of stacked catalyst arrangements include: HDS/ASAT/sorbent/RO; HDS/RO/ASAT; sorbent/ASAT/RO; and HDS/sorbent/ASAT/RO. Preferred mixed bed catalyst arrangements include: RO+ASAT; sorbent+RO; sorbent+ASAT+RO; and sorbent+HDS+RO. Conditions favoring the ring opening function are preferred.

The ring opened product may be recovered after the final processing step, i.e., after ring opening, after an optional ASAT final step, or after any further optional treatment step according to conventional methods. The recovered product may be used directly as, for example, a diesel fuel, jet fuel, gas oil, and heating oil, and it may be blended with other petroleum products and used as, for example, a diesel fuel, jet fuel, gas oil, and heating oil. When blended, it is preferred that the ring opened product be blended with a petroleum stream having an average boiling point of about 175° C. to about 600° C., wherein the blend has a cetane number of at least about 40.

The Periodic Table of the Elements referred to herein appears on the inside cover page of the Merck Index, 12th Ed., Merck & Co., 1996.

This invention will be better understood with reference to the following examples, which are intended to illustrate specific embodiments within the overall scope of the invention as claimed.

EXAMPLE 1

A ring opening catalyst comprising 0.9 wt. % Ir on an alumina support was prepared by impregnating alumina with chloroiridic acid from excess aqueous solution. The catalyst was dried under vacuum at 120° C. for 24 hr. The catalyst was charged to a reactor and reduced by hydrogen at 450° C. for 3 hr. The catalyst was used to ring open methylcyclohexane. The results are summarized in Table 1.

EXAMPLE 2

A sample of the catalyst from Example 1 after being dried at 120° C. for 24 hr was calcined in air at 270° C. for 3 hr. The catalyst was charged to a reactor and reduced by hydrogen at 450° C. for 3 hr. The catalyst was used to ring open methylcyclohexane. The results are summarized in Table 1.

EXAMPLE 3

A sample of the catalyst from Example 1 after being dried at 120° C. for 24 hr was calcined in air at 400° C. for 3 hr. The catalyst was charged to a reactor and reduced by hydrogen at 450° C. for 3 hr. The catalyst was used to ring open methylcyclohexane. The results are summarized in Table 1.

EXAMPLE 4

A ring opening catalyst comprising 0.9 wt. % Ir on an acidic silica-alumina molecular sieve, ECR-32, was prepared by incipient wetness impregnation with chloroiridic acid solution. The catalyst was dried under vacuum at 120° C. for 24 hr. The catalyst was charged to a reactor and reduced by hydrogen at 450° C. for 3 hr. The catalyst was used to ring open methylcyclohexane. The results are summarized in Table 1.

EXAMPLE 5

A ring opening catalyst comprising 0.9 wt. % Ir on an acidic silica-alumina molecular sieve, ECR-32, was prepared by incipient wetness impregnation with chloroiridic acid solution. The catalyst was dried under vacuum at 120° C. for 24 hr and was calcined in air at 400° C. for 3 hr. The catalyst was charged to a reactor and reduced by hydrogen at 450° C. for 3 hr. The catalyst was used to ring open methylcyclohexane. The results are summarized in Table 1.

EXAMPLE 6

A ring opening catalyst comprising 0.9 wt. % Ir on a composite substrate of alumina/silica-alumina molecular seive was prepared by impregnation with chloroiridic acid solution. The composite was prepared by intimately mixing powdered alumina with acidic silica-alumina molecular sieve, ECR-32. The mixture of alumina and silica-alumina molecular sieve was formed into particles suitable for Ir impregnation. The composite contained 80% alumina and 20% silica-alumina molecular sieve by weight. The catalyst was dried under vacuum at 120° C. for 24 hr and was calcined in air at 400° C. for 3 hr. The catalyst was charged to a reactor and reduced by hydrogen at 450° C. for 3 hr. The catalyst was used to ring open methylcyclohexane. The results are summarized in Table 1.

TABLE 1

Ring Opening Methylcyclohexane Over Ir Catalysts
(300° C., 200 psig, 10 W/H/W, $H_2$/Oil = 6)

| Example | 1 | 2 | 3 | 4 | 5 | 6 |
|---|---|---|---|---|---|---|
| Support | $Al_2O_3$ | $Al_2O_3$ | $Al_2O_3$ | Silica-Alumina | Silica-Alumina | $Al_2O_3$/Silica-Alumina |
| Air, ° C.-hr | 120-24 | 270-3 | 400-3 | 120-24 | 400-3 | 400-3 |
| Methane, Wt. % | 1.3 | 0.6 | 0.5 | 0.6 | 0.1 | 0.3 |
| $C_7$ Paraffin Yield, Wt. % | 30.0 | 19.1 | 17.2 | 53.8 | 6.9 | 31.3 |
| Cyclopentanes, Wt. % | 0.4 | 0.0 | 0.0 | 4.7 | 35.3 | 16.1 |
| Conversion, Wt. % | 41.9 | 24.2 | 21.7 | 72.4 | 47.3 | 56.1 |
| $C_7$ Paraffin Yield/$C_1$ Selectivity | 23.2 | 31.5 | 34.5 | 92.9 | 7.3 | 104.5 |

Examples 1–3 demonstrate the sensitivity of the Ir-on-alumina ring opening catalyst to calcination in air at temperatures greater than about 250° C. Activity and ring opening yield decrease by about 45% with incrementally higher deactivation at the higher temperature. Methane yield decreases by about 60%, and this improvement is measured by the higher ratio of ring opening yield selectivity to methane selectivity and reflects higher liquid to gas product selectivity.

Comparison of Example 4 with Example 1 shows that Ir supported on an acid silica-alumina molecular sieve is intrinsically a more active and selective catalyst than Ir-on-alumina, both catalysts having been dried at low temperature. The isomerization activity of acidic silica-alumina molecular sieve is evident in the presence of cyclopentanes surviving in the product, the greater fraction of these intermediates having been ring opened by Ir. Relative to Ir-on-alumina both activity and the yield of ring opened products increases by 80% over Ir on acidic silica-alumina molecular sieve. The methane yield decreases by about 50% to provide a high liquid/gas ratio.

Comparison of Examples 4 and 5 shows that Ir on acidic silica-alumina molecular sieve is more sensitive to calcination in air at high temperature than is Ir-on-alumina (Examples 1 and 2). Ring opening activity decreases by 87% following calcination of Ir/silica-alumina. Conversion remains relatively high as isomerization activity over Ir/silica-alumina remains high. While methane yield is significantly decreased, the selectivity of ring opened products to methane is poor due to deactivation of the ring opening function.

Example 6 for the catalyst of this invention shows that the composite catalyst is superior to all others despite having been calcined in air at 400° C. Activity and yield of the catalyst of Example 6 are exceeded only by Ir-on-silica-alumina in Example 4. However, the catalyst of Example 4 is deactivated upon calcination and cannot be regenerated by simple exposure to oxygen at high temperature. In addition, the catalyst of Example 6 affords a higher selectivity of liquids to gas. The catalyst of Example 6 is superior to the alumina based catalysts of Examples 1–3 in terms of activity, yield, and selectivity.

The catalyst of Example 6 demonstrates a synergy that imparts superior performance over its separate catalytic components of Examples 3 and 5 which is not expected. While not wishing to be bound by any theory, it is believed to arise from the distribution of Ir preferentially on the alumina component of the composite coupled with the isomerization activity of the acidic silica-alumina molecular sieve component, which converts methylcyclohexane to cyclopentanes. As the latter are more easily ring opened by Ir, substantial ring opening occurs over the composite even though Ir activity has been decreased by calcination. The relative ring opening and isomerization activities of Examples 2 and 5 support this hypothesis.

Having now fully described this invention, it will be appreciated by those skilled in the art that the invention can be performed within a wide range of parameters within what is claimed, without departing from the spirit and scope of the invention.

What is claimed is:

1. A naphthene ring opening catalyst system comprising:

a) a naphthene ring isomerizing catalyst containing a catalytically active naphthene ring isomerization metal supported on a first catalyst support in an amount effective to isomerze a $C_6$ naphthene ring-containing compound to a $C_5$ naphthene ring-containing compound; and b) a naphthene ring opening catalyst comprising Ir and on a composite support of alumina and acidic silica-alum molecular sieve,
   wherein the isomerizing catalyst and the ring opening catalyst are in a stacked bed arrangement.

2. The naphthene ring opening catalyst system of claim 1, wherein the isomerizing catalyst contains from about 0.1 to about 1.0 wt. % of at toast one of Pt and Pd, based on the weight of the isomerizing catalyst, and wherein the ring opening catalyst contains from about 0.01 to about 0.5 wt. % Ir, based on the weight of the ring opening catalyst.

3. The naphthene ring opening catalyst system of claim 2, wherein the isomerizing catalyst and the ring opening catalyst are present at a weight ratio of about 50:99 parts of the isomerizing catalyst to about 50:1 parts of the ring opening catalyst.

4. The naphthene ring opening catalyst system of claim 1, wherein the first support is at least one refractory inorganic oxide selected from the group consisting of alumina, silica, zirconia, titania, chromia, zinc oxide, magnesia, thoria, boria, silica-alumina, silica-magnesia, chromia-alumina, alumina-boria, and silica-zirconia.

5. The naphthene ring opening catalyst system of claim 4, wherein the refractory inorganic oxide is alumina, and wherein the acidic silica-alumina molecular sieve has a Si/Al atomic ratio of at least about 30.

6. The naphthene ring opening catalyst of claim 1, wherein the alumina in the ring opening catalyst's support is present in a range of from about 99 to about 1 wt. %, and the acidic silica-alumina molecular sieve in the ring opening catalyst's support is present in a range of from about 1 to about 99 wt %.

7. The naphthene ring opening catalyst of claim 1, wherein Ir is present in a range of from about 0.01 to about 2.0 wt.%, and wherein the second Group VIII metal is present in a range of from about 0.01 to about 5 wt. %.

* * * * *